United States Patent [19]

Thelen et al.

[11] Patent Number: 5,391,750
[45] Date of Patent: Feb. 21, 1995

[54] PROCESS FOR THE PREPARATION OF 4-HYDROXY-2,2,6,6-TETRAMETHYL-PIPERIDINE

[75] Inventors: Gerhard Thelen, Nottuln; Guthard Mock; Otto Hallmann, both of Marl, all of Germany

[73] Assignee: Huels Aktiengesellschaft, Marl, Germany

[21] Appl. No.: 154,040

[22] Filed: Nov. 18, 1993

[30] Foreign Application Priority Data

Nov. 21, 1992 [DE] Germany .............. 4239247

[51] Int. Cl.⁶ .......................... C07D 211/36
[52] U.S. Cl. ...................... 546/242; 546/243
[58] Field of Search ................. 546/242, 243

[56] References Cited

U.S. PATENT DOCUMENTS

| | | | |
|---|---|---|---|
| 4,001,250 | 1/1977 | Lantzsch et al. | 546/242 |
| 4,339,585 | 7/1982 | Matsumura et al. | 546/242 |
| 4,910,304 | 3/1990 | Fischer et al. | 546/242 |

*Primary Examiner*—C. Warren Ivy
*Assistant Examiner*—Raymond Covington
*Attorney, Agent, or Firm*—Oblon, Spivak, McClelland, Maier & Neustadt

[57] ABSTRACT

The present invention relates to a process for the preparation of 4-hydroxy-2,2,6,6-tetramethylpiperidine by heterogeneous catalytic hydrogenation of 4-oxo-2,2,6,6-tetramethylpiperidine in a melt or solution at temperatures of 60° C. to 200° C. and hydrogen pressures of 10 to 300 bar, in the presence of a catalyst comprising from 20 to 68% by weight of copper,
from 0 to 40% by weight of chromium,
from 0 to 60% by weight of zinc,
from 0 to 5% by weight of manganese,
from 0 to 12% by weight of barium,
from 0 to 15% by weight of silicon, and
from 0 to 10% by weight of nickel, in each case based on the oxidic catalyst mass, and in which the catalyst is activated by hydrogen or a hydrogen-containing gas mixture, and separating the 4-hydroxy-2,2,6,6-tetramethylpiperidine from the catalyst.

14 Claims, No Drawings

PROCESS FOR THE PREPARATION OF 4-HYDROXY-2,2,6,6-TETRAMETHYLPIPERIDINE

BACKGROUND OF THE INVENTION

1. Field of the Invention

The present invention describes a method for the hydrogenation of 4-oxo-2,2,6,6-tetramethylpiperidine (triacetoneamine, TAA) to give 4-hydroxy-2,2,6,6-tetramethylpiperidine (TTA-ol) and a catalyst suitable for use in the method. The catalyst can be arranged as a fixed bed in a continuous process, and can be used discontinuously as a powder in a batch process, in accordance with the present invention.

2. Discussion of the Background

Numerous catalysts are known from the literature for the preparation of 4-hydroxy-2,2,6,6-tetramethylpiperidine. For example, the use of nickel catalysts is described in Czechoslovak Patent Nos. 235,486, 235,487 and 236,437. TAA is used in each case as an alcoholic solution (for example, in isopropanol and isobutanol). Other catalyst-solvent combinations are mentioned in other patent documents. In DE-A 2,656,765, Ciba Geigy proposes the use of nickel catalysts and noble metal catalysts in the solvents such as toluene, xylene and ethers; in DE-A 2,656,764, Ni and Ru as catalyst and water as solvent; in DE-A 2,656,763, Ni and noble metals (Ru, Rh, Os, Ir, Pt) as catalyst metals and tri-n-alkyl phosphates as solvents; in EP-A 225,850 and EP-A 375,612, Ru as catalyst and water or alcohols as solvent. Finally, EP-A-290,387 claims a hydrogenation process in the presence of a metal catalyst selected from the group comprising Ni, Co, Ru, Rh, Os and Ir, in the absence of a solvent. Ni and Ru catalysts are preferred.

Previous processes for the hydrogenation of TAA to give TAA-ol are known to have considerable disadvantages. Such disadvantages include complex procedures required for the separation of by-products, waste water pollution and losses of both product and solvent.

From both ecological and economic points of view, it is necessary that the hydrogenation of TAA to give TAA-ol proceeds with complete conversion and very high selectivity. When these conditions are met, the losses of TAA-ol are small, and only very small quantities of by-products are formed. As a result, solvents (if present) can be completely recycled.

SUMMARY OF THE INVENTION

Accordingly, one object of the present invention is to provide a novel method for the hydrogenation of TAA which provides TAA-ol with essentially complete conversion.

It is a further object of the present invention to provide a novel method for producing TAA-ol from TAA with very high selectivity.

It is a further object of the present invention to provide a novel method for producing TAA-ol from TAA which permits essentially complete recycling of solvents.

It is a further object of the present invention to provide a novel method for producing TAA-ol from TAA in which a small proportion of by-products is formed.

It is a further object of the present invention to provide a novel method for producing TAA-ol from TAA in which the product losses are small.

It is a further object of the present invention to provide a novel method for producing TAA-ol from TAA in which waste water pollution is minimized.

It has surprisingly been found that the hydrogenation of TAA to give TAA-ol in the presence of a copper catalyst proceeds with very high selectivity, thus preventing the known disadvantages of previous processes for the hydrogenation of TAA to give TAA-ol. The advantages of the present invention are particularly apparent when the hydrogenation is carried out in the absence of a solvent.

These and other objects of the present invention, which will become apparent during the following detailed description of the preferred embodiments, have been provided a method for the hydrogenation of 4-oxo-2,2,6,6-tetramethylpiperidine in a melt or in solution at temperatures of 60° C. and 200° C. and hydrogen pressures of 10 to 300 bar, in the presence of a catalyst which comprises:

from 20 to 68% by weight of copper,
from 0 to 40% by weight of chromium,
from 0 to 60% by weight of zinc,
from 0 to 5% by weight of manganese,
from 0 to 12% by weight of barium,
from 0 to 15% by weight of silicon, and
from 0 to 10% by weight of nickel, in each case based on the oxidic catalyst mass, and in which the catalyst is activated by hydrogen or a hydrogen-containing gas mixture.

DETAILED DESCRIPTION OF THE PREFERRED EMBODIMENTS

The copper catalysts according to the present invention are activated by addition of further metals. Preference is given to Cr, Mo, W, Mn, Re, Fe, Co, Ni, Zn, Ba and Si. According to the present invention, the copper catalysts are used in a conventional form; that is, the catalytically active metals are used as so-called "complete" catalysts, in the form of granules, extrudates or tablets, or applied to support materials as supported catalysts. "Complete" catalysts refer to catalysts which can be used for their intended purpose as is, and which are either catalytically active or become catalytically active while in use.

The present catalyst may be supported on a conventional inert support material. Supports which are useful are commercially available, insoluble substances, such as activated charcoal, silica gel, aluminum oxide, etc.

For continuous hydrogenation, the preferred form of the present catalyst is a disc-shaped tablet having dimensions of from 3 mm in diameter by 3 mm in thickness (3 mm×3 mm), up to 9 mm×9 mm, and in particular, from 3 mm×3 mm to 6 mm×6 mm. A cylindrical extrudate having a diameter of 1 mm to 5 mm is also an acceptable form for the present catalyst. The preferred form of the present catalyst for batch hydrogenation is powder.

The present copper catalyst contains from 20% to 68% by weight of copper. One or more promoters may be present. When used as a promoter, chromium is added in a range of from 0% to 40% by weight, manganese in a range of from 0% to 5% by weight, barium in a range of from 0% to 12% by weight, silicon in a range of from 0% to 15% by weight, nickel in a range of from 0% to 10% by weight and zinc in a range of from 0% to 60% by weight, in each case based on the total mass of the oxidic catalyst. The "oxidic catalyst mass" and the "total mass of the oxidic catalyst" refer to the total weight or mass of the catalyst, in which the metals are present in an oxidized form. In the present catalyst, the metals are presumed to be present as the corresponding oxide, and the percentage of each metal present is calculated as the weight % of the metal present in the catalyst.

In a preferred embodiment, the present catalyst comprises from 26% to 41% of copper, from 24% to 38% of chromium, from 0% to 4% of manganese and from 0% to 12% of barium, based on the oxidic catalyst mass. The specific surface area of the catalyst of this preferred embodiment, as determined by the BET (Brunauer-Emmett-Teller) method, is from 10 to 60 m$^2$/g. The pore volume is preferably between 0.1 and 0.5 cm$^3$/g.

In a further preferred embodiment, the present catalyst comprises from 20% to 65% of copper and from 20% to 60% of zinc, preferably from 22 to 28% of copper and from 49 to 55% of zinc, based on the oxidic catalyst mass. The specific surface area (BET) of this embodiment is preferably from 30 to 70 m$^2$/g, and the pore volume is preferably from 0.2 to 0.5 cm$^3$/g.

The present supported copper catalyst comprises from 30% to 80% of a support material, 10% to 40% of copper, from 0% to 15% of chromium, from 0% to 5% of barium and from 0% to 20% of iron (calculated as $Fe_2O_3$). The specific surface area of the supported catalyst, as determined by the BET method, is preferably from 10 to 250 m$^2$/g. The pore volume is preferably between 0.1 and 0.9 cm$^3$/g. The preferred support material is silica gel or aluminum oxide.

Suitable catalysts for the present method include those available commercially under the tradenames "G99B," "T2130," and "G99B-13," manufactured by Südchemis, Munich, Germany; under the tradenames "H1117T," "B708A-E3164," and "Cu 1803P," manufactured by Engelhard, DeMeern, Netherlands; and under the tradename "H1201," manufactured by Hüls, Marl, Germany.

The present invention also concerns a method for for the preparation of 4-hydroxy-2,2,6,6-tetramethylpiperidine, comprising:

contacting 4-oxo-2,2,6,6-tetramethylpiperidine with hydrogen gas and a catalyst comprising from 20 to 68% by weight of copper, from 0 to 40% by weight of chromium, from 0 to 60% by weight of zinc, from 0 to 5% by weight of manganese, from 0 to 12% by weight of barium, from 0 to 15% by weight of silicon, and from 0 to 10% by weight of nickel, in each case based on the oxidic catalyst mass, in a melt or solution at a temperature of from 60° C. to 200° C. and a hydrogen pressure of from 10 to 300 bar; and separating the 4-hydroxy-2,2,6,6-tetramethylpiperidine from the catalyst.

Hydrogen gas may be present as a mixture of gases which contains hydrogen. The mixture of gases preferably contains hydrogen gas and at least one inert gas. Inert gases suitable for use in the present method include dinitrogen, helium, neon, and argon gases.

The present hydrogenation is expediently carried out at a temperature of from 60° C. to 200° C., preferably from 80° C. to 180° C. In the case of discontinuous or batch-wise hydrogenation, the reaction is preferably started at a low temperature, in particular from 60° to 80° C. The temperature is then increased to a temperature of from 120° to 150° C., in particular from 130° to 150° C., and is then held constant until the reaction is complete.

Continuous hydrogenation according to the present invention is preferably carried out at constant temperature, for example from 120° to 180° C., and preferably, from 140° to 170° C. In this case, the copper catalysts are used as a fixed bed, and filtration of the catalyst is not necessary.

As a result of the high selectivity which is achieved by the present copper catalysts and method, the product TAA-ol is highly pure. The present copper catalysts provide a significant increase in the space-time yield of product, in comparison to previously known catalysts and processes.

The reaction of TAA proceeds in the presence of the present copper catalysts at hydrogen pressures of from 10 to 300 bar. In the case of discontinuous hydrogenation, hydrogen is used in the pressure range from 10 to 100 bar, preferably at 20 to 95 bar. The continuous preparation of TAA-ol is carried out in a pressure range of from 10 to 300 bar. Plants (bulk chemical production facilities and apparatuses) in the high pressure range conventionally operate at 150 to 300 bar, and thus, conventional high-pressure chemical production plants are particularly suitable for the present continuous process for producing TAA-ol. The conversion of TAA to TAA-ol can also be carried out at 10 to 100 bar, preferably at 20 to 95 bar, with the advantages mentioned.

The present method for producing TAA-ol by hydrogenating TAA may be performed under the conditions mentioned above in the presence of a $C_1$–$C_{10}$ alcohol as solvent, preferably a $C_4$–$C_8$ alcohol, such as isobutanol, n-butanol, and 2-ethylhexanol. However, the present hydrogenation of TAA is advantageously carried out in the absence of a solvent.

The hydrogenation time varies, and depends on the particular catalyst used, on the catalyst concentration, on the hydrogen pressure and on the reaction temperature. The reaction time is thus determined empirically, and typically, the reaction time can be from 1 minute to 2 hours. When the present catalyst is used as a fixed bed, volumetric rates (liquid hourly space velocity, or LHSV) of 0.5 to 3 h$^{-1}$, in particular 0.5 to 1.5 h$^{-1}$, are expected. LHSV is defined as follows:

$$LHSV = \frac{\text{Rate of starting material introduction (liters/hour)}}{\text{Amount of catalyst (liters)}}$$

In the present discontinuous process, the catalyst is used in an amount of 0.1 to 3% by weight, preferably 0.1 to 2% by weight, in particular 0.2 to 1.5% by weight, based on the volume of TAA used.

4-Hydroxy-2,2,6,6-tetramethylpiperidine is an important intermediate for the preparation of sterically hindered amine stabilizers. Such stabilizers are typically used to protect various compositions (such as polymers, polymer blends, composite materials, dyestuffs, etc.) from damage typically induced by or associated with heat, light, radical sources (such as singlet oxygen or ozone, etc.).

Other features of the invention will become apparent in the course of the following descriptions of exemplary embodiments which are given for illustration of the invention and are not intended to be limiting thereof. The examples below are intended to illustrate the present invention.

CATALYST EXAMPLES

Example 1

The catalyst type I contained 36% by weight of copper, 32% by weight of chromium, 2.5% by weight of barium and 2.5% by weight of manganese, the balance containing oxygen (in the form of the corresponding methal oxides). This catalyst is available commercially under the tradename "G99B," manufactured by Südchemic, Munich, Germany. Tablets of the catalyst type I having the dimensions 3×3 mm were made. The surface area was approximately 30 cm²/g.

Example 2

The catalyst type II contained 27% by weight of copper, 25% by weight of chromium and 7% by weight of barium. This catalyst is available commercially under the tradename "H1117T," manufactured by Engelhard, DeMeern, Netherlands. The catalyst, in the form of tablets of ⅛"×150" dimensions, had a surface area of approximately 30 m²/g.

Example 3

As an example of a CuZn type catalyst (catalyst type III), an oxidic mass composed of 26% by weight of copper and 53% by weight of zinc in the form of 3×3 mm tablets was prepared and tested. This catalyst is available commercially under the tradename "T2130," manufactured by Südchemic, Munich, Germany. The catalyst had a surface of 45 m²/g.

Example 4

The supported catalyst type IV contained, in addition to 57% by weight of silica gel as support material, 23.0% by weight of copper and 4.2% by weight of iron. This catalyst is available commercially under the tradename "B708A-E3164," manufactured by Engelhard, DeMeern, Netherlands. The oxidic mass was prepared in the form of an extrudate having a diameter of 1.2 mm and a BET surface area of 210 m²/g.

Example 5

A catalyst type V having a chemical composition of 62% by weight of $SiO_2$, 21.3% by weight of copper, 4.5% by weight of barium and 2.0% by weight of chromium, available commercially under the tradename "H1201," manufactured by Hüls, Marl, Germany, was prepared as an extrudate having a diameter of 4 mm, and a BET surface area of 130 m²/g.

Example 6

The powder catalyst type VI was composed of 40.8% by weight of copper and 31.6% by weight of chromium, in each case based on the oxidic mixture. In this example, 40.8% by weight of copper corresponds to 51% by weight of CuO, and 31.6% by weight of chromium corresponds to 46.7% by weight of $Cr_2O_3$. Therefore, the powder catalyst type VI is composed essentially of oxides of copper and chromium, in the proportions by weight of metal mentioned above. This catalyst is available commercially under the tradename "Cu 1803P," manufactured by Engelhard, DeMeern, Netherlands. The surface area of the catalyst was 42 m²/g.

Example 7

The powder catalyst type VII was composed of 36.5% by weight of copper and 32% by weight of chromium and 0.5% by weight of barium and 4% by weight of manganese. This catalyst is available commercially under the tradename "G99B-13," manufactured by Südchemic, Munich, Germany. The surface area was 30 m²/g.

PROCESS EXAMPLES

Continuous hydrogenation

A test plant for high pressure hydrogenation contained a hydrogen gas pressure valve, a reservoir for TAA, a transport pump for supplying TAA to the reactor, a 400 ml reactor and a separation vessel for isolating the product. The reactor is completely filled with 400 ml of the copper catalyst.

As shown in Table I below, a series of hydrogenation reactions were conducted in the complete apparatus under an $H_2$ pressure of p bar, in which the reactor was operated at a temperature T. The product obtained was analyzed by gas chromatography.

The results with each of the catalysts I–V are listed in Table I below.

TABLE I

| Example | Catalyst type | Reaction pressure p (bar) | Reaction temperature (°C.) | LHSV ($h^{-1}$) | TAA Conversion Rate (molar %) | Selectivity TAA-ol (molar %) |
| --- | --- | --- | --- | --- | --- | --- |
| 1 | I | 300 | 150 | 1 | >99.9 | >99 |
| 2 | I | 300 | 170 | 1 | >99.9 | >99 |
| 3 | I | 150 | 170 | 0.8 | >99.9 | >99 |
| 4 | II | 300 | 170 | 1 | >99.9 | >99 |
| 5 | III | 300 | 170 | 1 | >99.9 | >99 |
| 6 | III | 150 | 170 | 1 | >99.9 | >99 |
| 7 | IV | 300 | 170 | 0.5 | >99 | >99 |
| 8 | V | 300 | 160 | 0.8 | >99 | >99 |

Discontinuous hydrogenation

A 1 liter autoclave was used for the discontinuous batchwise hydrogenation. To carry out each of the tests, 400 ml of TAA was introduced into the autoclave, a predetermined amount of the powder catalyst of either type VI or type VII was added, the mixture was heated to reaction temperature $T_1$, a reaction pressure p was established and then the mixture was held at a temperature of $T_2$. After releasing excess pressure, the product was separated from the catalyst by filtration, using a frit. The purity of the product was analyzed by gas chromatography. The data are shown below in Table II.

TABLE II

| Example | Catalyst type | Reaction pressure p (bar) | Reaction temperature T$_1$ (°C.) | T$_2$ (°C.) | Concentration of catalyst (g/l) | TAA Conversion Rate (molar) | Selectivity TAA-ol (molar %) |
|---------|---------------|---------------------------|------------------|------------------|---------------------------------|------------------------------|------------------------------|
| 9       | VI            | 90                        | 70               | 150              | 10                              | >99                          | >99                          |
| 10      | VII           | 90                        | 80               | 150              | 12                              | >99                          | >99                          |

Example 11

A solution, composed of 50 parts of TAA and 50 parts of isobutanol, was continuously hydrogenated on a fixed-bed catalyst of type I at a temperature of 145° C., a reaction pressure of 300 bar and at a LHSV +0.8 h$^{-1}$. The gas-chromatographic analysis of the product gave a TAA conversion rate >99.9 molar % and a selectivity to TAA-ol of > 99 molar %.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method for the preparation of 4-hydroxy-2,2,6,6-tetramethylpiperidine, comprising:
    contacting 4-oxo-2,2,6,6-tetramethylpiperidine with hydrogen gas and a catalyst comprising from 20 to 68% by weight of copper, from 0 to 40% by weight of chromium, from 0 to 60% by weight of zinc, from 0 to 5% by weight of manganese, from 0 to 12% by weight of barium, from 0 to 15% by weight of silicon, and from 0 to 10% by weight of nickel, in each case based on the oxidic catalyst mass, in a melt or solution at a temperature of from 60° C. to 200° C. and a hydrogen pressure of from 10 to 300 bar; and
    separating said 4-hydroxy-2,2,6,6-tetramethylpiperidine from said catalyst.

2. The method of claim 1, wherein said catalyst contains:
    from 26 to 41% by weight of copper,
    from 24 to 38% by weight of chromium,
    from 0 to 4% by weight of manganese, and
    from 0 to 12% by weight of barium.

3. The method of claim 1, wherein said catalyst contains:
    from 20 to 65% by weight of copper, and
    from 20 to 60% by weight of zinc.

4. The method of claim 3, wherein said catalyst contains:
    from 22 to 28% by weight of copper, and
    from 49 to 55% by weight of zinc.

5. The method of claim 1, wherein said catalyst is activated by hydrogen.

6. A method for the preparation of 4-hydroxy-2,2,6,6-tetramethylpiperidine, comprising:
    contacting 4-oxo-2,2,6,6-tetramethylpiperidine with hydrogen gas and a supported catalyst comprising from 30 to 80 % by weight of support material, from 10 to 40% by weight of copper, from 0 to 15% by weight of chromium, from 0 to 5% by weight of barium, and from 0 to 20% by weight of iron, in each case based on the oxidic catalyst mass, in a melt or solution at a temperature of from 60° C. to 200° C. and a hydrogen pressure of from 10 to 300 bar; and
    separating said 4-hydroxy-2,2,6,6-tetramethylpiperidine from said catalyst.

7. The method of claim 6, wherein said catalyst is activated by hydrogen.

8. The method of claim 6, wherein said support material is activated charcoal, silica gel or aluminum oxide.

9. The method of claim 6, wherein said support material is silica gel.

10. The method of claim 1, wherein said hydrogen gas is present as a mixture of gases.

11. The method of claim 10, wherein said mixture of gases comprises said hydrogen gas and at least one inert gas.

12. The method of claim 6, wherein said mixture of gases comprises said hydrogen gas and at least one inert gas.

13. The method of claim 1, wherein said catalyst is selected from the group consisting of (a) a catalyst containing 36 wt. % copper, 32 wt. % chromium, 2.5 wt. % barium and 2.5 wt. % manganese, (b) a catalyst containing 27 wt. % copper, 25 wt. % chromium and 7 wt. % barium, (c) a catalyst containing 26 wt. % copper and 53 wt. % zinc, (d) a catalyst containing 23 wt. % copper and 4.2 wt. % iron, (e) a catalyst containing 21.3 wt. % copper, 4.5 wt. % barium and 2.0 wt. % chromium, (f) a catalyst containing 40.8 wt. % copper and 31.6 wt. % chromium, and (g) a catalyst containing 36.5 wt. % copper, 32 wt. % chromium copper, 0.5 wt. % barium and 4 wt. % manganese.

14. The method of claim 6, wherein said catalyst is selected from the group consisting of (a) a catalyst containing 36 wt. % copper, 32 wt. % chromium, 2.5 wt. % barium and 2.5 wt. % manganese, (b) a catalyst containing 27 wt. % copper, 25 wt. % chromium and 7 wt. % barium, (c) a catalyst containing 26 wt. % copper and 53 wt. % zinc, (d) a catalyst containing 23 wt. % copper and 4.2 wt. % iron, (e) a catalyst containing 21.3 wt. % copper, 4.5 wt. % barium and 2.0 wt. % chromium, (f) a catalyst containing 40.8 wt. % copper and 31.6 wt. % chromium, and (g) a catalyst containing 36.5 wt. % copper, 32 wt. % chromium copper, 0.5 wt. % barium and 4 wt. % manganese.

* * * * *